United States Patent [19]

Botré et al.

[11] 4,192,894

[45] Mar. 11, 1980

[54] COMPOUND WITH DISINFECTANT ACTIVITY AND PHARMACEUTICAL COMPOSITIONS CONTAINING THE SAME

[75] Inventors: Claudio Botré; Franco Bolasco; Adriana Memoli, all of Rome; Luigi Molteni, Malnate, all of Italy

[73] Assignee: Dr. L.° Zambeletti S.p.A., Baranzate, Italy

[21] Appl. No.: 829,586

[22] Filed: Aug. 31, 1977

[30] Foreign Application Priority Data

Aug. 7, 1977 [IT] Italy .................................. 41006 A/77

[51] Int. Cl.$^2$ .......................... C07C 87/68; A01N 9/16
[52] U.S. Cl. ............................. 424/329; 260/567.6 M
[58] Field of Search ............... 260/567.6 M, 567.6 R, 260/567.6 F, 567.6 H; 424/329

[56] References Cited

U.S. PATENT DOCUMENTS

| 3,152,073 | 10/1964 | Morton | 260/567.6 M |
| 3,279,981 | 10/1966 | Geiger et al. | 260/567.6 F |

FOREIGN PATENT DOCUMENTS

| 948966 | 6/1962 | United Kingdom | 260/567.6 M |
| 1155258 | 11/1967 | United Kingdom | 260/567.6 M |

*Primary Examiner*—James H. Reamer
*Attorney, Agent, or Firm*—Haseltine, Lake & Waters

[57] ABSTRACT

This invention provides an iodinated derivative of benzalkonium chloride having antiseptic activity combined with a lower toxicity than the corresponding chloride.

2 Claims, No Drawings

COMPOUND WITH DISINFECTANT ACTIVITY AND PHARMACEUTICAL COMPOSITIONS CONTAINING THE SAME

The subject of this invention is a new compound with disinfectant activity.

According to the invention we provide as a new compound an iodinated derivative of benzalkonium chloride having antiseptic and disinfectant action of average molecular formula $C_{22}H_{40}Cl_2IN$ referred to herein as benzalkonium chloroiodite. It is of course well known that "benzalkonium" is the normally used name of the alkyl dimethylbenzylammonium cation, where the alkyl group is a mixture of $C_8H_{17}$—$C_{18}H_{37}$ groups with a median value $C_{13}H_{27}$.

Benzalkonium chloroiodite possesses features which render it advantageous for use in therapy as a drug having a high activity against both gram-positive and gram-negative bacteria, against yeast and against mycetes. The present invention thus also provides pharmaceutical compositions with antiseptic or disinfectant action containing as an active principle benzalkonium chloroiodite.

According to this invention, benzalkonium chloroiodite may be prepared by reaction of benzalkonium chloride with at least a stoichiometric amount of iodine and with at least a stoichiometric amount of chlorine. Iodine and chlorine may be used as such or may be formed in situ; for instance, chlorine may be generated from an alkali metal chlorate and hydrochloric acid, and iodine from an alkali metal iodide and chlorine.

The toxicity and the bactericidal activity of benzalkonium chloroiodite were compared with those of benzalkonium chloride conventionally used as an antiseptic.

1. Acute Toxicity

The acute toxicity was determined by orally administering benzalkonium chloride to mice. $LD_{50}$ were calculated by the graphic method of Lichtfield and Wilcoxon (J. Pharm. Exptl. Therap. 96, 99 (1949)). It was found that the $LD_{50}$ was 569 mg/kg when using benzalkonium chloride and 1272 mg/kg when using benzalkonium chloriodite. Thus, the compound according to the invention is much less toxic than the corresponding chloride.

2. Bactericidal Activity

The bactericide activity has been studied on two microbic species:
(1) *Staphylococcus Aureus* ATCC 6538P (gram-positive)
(2) *Escherichia Coli* ATCC 15153 (gram-negative).

The microbes are maintained at 4° C. in the means of solid maintenance Tryptic Soy Agar (Difco).

One day before use, a loopful of bacterial agar coating is transferred into Tryptic Soy Broth and incubated at 37° C. for 18 hours. At the moment of use, the suspension is brought to a transmittance of 87.5% read on a Spekol spectrocolorimeter; and is then diluted 1 to 10 with physiological solution.

The test is effected on a solid medium on plates. The culture medium Tryptic Soy Agar, previously sterilized in an autoclave at one atmosphere for 15 minutes, is poured onto each plate and allowed to cool to form the base plates.

A further 200 ml portion of medium which has been sterilised and cooled at 47° C. in a water bath, is seeded with 1 ml of the bacterial suspension previously prepared (Seed) and poured on the base plates. On the solidified surface are placed following a randomized scheme, small steel cylinders (diameter 0.6 mm) into which are introduced 0.2 ml aliquots of the solution to be tested. The plates are then left to diffuse in a refrigerator at 4° C. for 24 hours and are then incubated in thermostat at 37° C. for 18 hours.

The bactericidal activity of benzalkonium chloriodite and benzalkonium chloride was calculated by using increasingly higher concentrations of the two products so as to obtain a linear serial dilution dose response (zones of inhibition of growth of the microorganisms). From these values, straight lines of regression were calculated by plotting the concentrations used for each product on the abscissa and the inhibition values which were obtained for each dose used on the ordinate.

After calculation of the statistical validity of such regressions for each pair of straight lines obtained, the parallelism which is the essential condition for calculating the relative activity between the two studied substances was subsequently studied. (Bliss C. C. "The Statistics of Bioassay" Academic Press N.Y., 1952).

Preparation of the Solutions

Equimolar quantities of the two products were weighed.

Benzalkonium Chloride
(1) 10 mg/10 ml=28.3 μmol./ml
(2) 5 ml(1)/10 ml=14.15 μmol./ml
(3) 5 ml(2)/10 ml=7.07 μmol./ml
(4) 5 ml(3)/10 ml=3.54 μmol./ml
(5) 5 ml(4)/10 ml=1.77 μmol./ml
(6) 5 ml(5)/10 ml=0.885 μmol./ml Benzalkonium Chloroiodite
(1) 17.1 mg/10 ml=28.3 μmol./ml
(2) 5.0 ml(1)/10 ml=14.15 μmol./ml
(3) 5.0 ml(2)/10 ml=7.07 μmol/ml
(4) 5.0 ml(3)/10 ml=3.54 μmol/ml
(5) 5.0 ml(4)/10 ml=1.77 μmol/ml
(6) 5.0 ml(5)/10 ml=0.88 μmol/ml The results are reported in Table 1

TABLE 1

| | | Zones of inhibition of microorganism (in mm) growth at the following concentrations of product expressed in μmol./ml | | | | | | Relative potency |
|---|---|---|---|---|---|---|---|---|
| Microorganisms | Product | 0.885 | 1.77 | 3.54 | 7.07 | 14.15 | 28.30 | |
| *Staphylococcus Aureus* ATCC 6538P | Benzalkonium Chloride | 14.6 | 17.0 | 19.6 | 21.8 | 25.7 | 27.0 | |
| | | | | | | | | 4.5 |
| | Benzalkonium Chloroiodite | 20.5 | 22.8 | 25.1 | 27.3 | 29.6 | 31.9 | |
| | Benzalkonium | — | 13.9 | 15.9 | 18.1 | 20.0 | 22.9 | |

TABLE 1-continued

| | | Zones of inhibition of microorganism (in mm) growth at the following concentrations of product expressed in μmol./ml | | | | | | |
|---|---|---|---|---|---|---|---|---|
| Microorganisms | Product | 0.885 | 1.77 | 3.54 | 7.07 | 14.15 | 28.30 | Relative potency |
| | Chloride | | | | | | | 9.4 |
| Echerichia coli ATCC 15153 | Benzalkonium Chloroiodite | 18.0 | 21.2 | 23.5 | 25.4 | 26.8 | 28.5 | |

The following tables refer to the antifungal and microbicidal activities of the compound according to the invention.

TABLE II

Antifungal and antibacterial activity of Benzalkonium Chloroiodite

| Species | minimum inhibitory concentration (per 100 ml) | Minimum lethal concentration (per 100 ml) |
|---|---|---|
| S. aureus | 61 μg | 480 μg |
| B. subtilis | 61 μg | 180 μg |
| E. coli | 3.9 mg | 15.6 mg |
| Ps. aeruginosa | 31.2 mg | 62.5 mg |
| Asp. niger | 970 μg | 970 μg |
| C. albicans | 480 μg | 970 μg |

TABLE III

Microbicidal activity of benzalkonium chloroiodite on bacteria and mycetes (at minimum lethal concentration)

| Species | Time |
|---|---|
| S. aureus | 1 min |
| B. subtilis | 1 min |
| E. coli | 1 min |
| Ps. aeruginosa | 1 min |
| Asp. niger | 1 min |
| C. albicans | 1 min |

The substance which is the subject of this invention may appropriately be formulated in pharmaceutical forms for administration in human and veterinary medicine.

The choice of the excipient is determined by the pharmaceutical form and by the standard pharmaceutical practice. Particularly preferable formulations include nebulized disinfectant solutions or sprays, orally antiseptic chewing-gums, orally antiseptic drops, antiseptic solutions for disinfecting small wounds and solutions for use in disinfectant cloths.

The following non-limitative Examples illustrate the invention further.

EXAMPLE 1

In a three-necked round-bottomed flask provided with a reflux condenser, stirrer and a bubbling tube a determined quantity of benzalkonium chloride (35 g) was dissolved in the minimum of $H_2O$ necessary.

Iodine was added in a slight excess (14 g) with respect to the stoichiometric quantity and the mixture was kept at room temperature for a few minutes.

Chlorine was then passed into the solution through the bubbling tube. The reaction product, insoluble in an aqueous medium, separated as it was formed. The reaction was allowed to continue to completion with stirring and with bubbling of chlorine for 15 hours (the time is variable from 12 to 24 hours depending on the initial quantities of reagents).

The yellow product which developed, of gummy consistency, was filtered off under vacuum, washed repeatedly over a filter with cold $H_2O$ and subsequently dried.

It was crystallized from methyl alcohol to obtain a yellow crystalline product of m.p.=80°-81° C., stable during the time it was studied.

The yield is 42.8 g (90%). The purity and the constitution are confirmed by the elemental analysis (see below).

EXAMPLE 2

Equivalent quantities of benzalkonium chloride (71 g) and iodine (26 g) were brought into aqueous solution (rendered acid with hydrochloric acid) in sufficient water to dissolve the benzalkonium chloride at 60° C. Bubbling of chlorine into the solution was then started. During the course of the reaction the product in form of a heavy yellow suspension separated. The mixture was agitated for 18 hours, with chlorine being passed.

At the end of the reaction, the mixture was allowed to rest for a further 12 hours in order to obtain a better separation of the suspension. It was then decanted and the precipitate extracted with chloroform. The chloroform solution was concentrated to dryness and the yellow solid obtained was crystallized from methyl alcohol.

This method gives a yield of 80% of the product, the purity and constitution of which are confirmed by the elemental analysis (see below).

EXAMPLE 3

Stoichiometric quantities of benzalkonium chloride (35.3 g) and iodine (13 g) were introduced into a quantity of water sufficient to dissolve the benzalkonium chloride.

To the mixture there was then added such quantity of $KClO_3$ and HCl as to provide a stoichiometric quantity of chlorine as regards the benzalkonium chloride and iodine (2.1 g and 3.7 g respectively).

The mixture was kept under continuous agitation while the reaction container is cooled with running water.

The reaction product separated slowly as a heavy yellow powder. Agitation was continued until disappearance of chlorine in the solution. The product was then filtered off, washed with iced water, dried and crystallized from methanol in 75% yield. The purity and the constitution of the product are confirmed by the elemental analysis (see below).

EXAMPLE 4

Equivalent quantities of benzalkonium chloride (35.3 g) and sodium iodide (15 g) were introduced into a quantity of water sufficient to dissolve them at 40° C.

Bubbling of chlorine through the solution was then commenced, thus liberating iodine forming iodine trichloride which reacted, as it was formed, with the benzalkonium chloride to form the desired product which precipitated as an amorphous yellow mass.

The reaction was allowed to preceed to completion with agitation and with bubbling chlorine for 24 hours. The product was filtered off was subsequently washed with cold water dried and crystallized from methanol.

Yield: 70%. The purity and the constitution of the product are confirmed by the elemental analysis.

The elementary analysis of the product obtained in the above Examples gave the following typical results:

|    | Calculated | Found |
|----|------------|-------|
| C% | 51.16      | 51.6  |
| H% | 7.80       | 7.5   |
| Cl%| 13.70      | 13.2  |
| I% | 24.54      | 24.2  |
| N% | 2.71       | 2.8   |

The above examples are not limiting because, as indicated, there may be used any reagent, potentially able to liberate iodine, e.g. by action of chlorine, and any other source of chlorine.

EXAMPLE 5

Disinfectant Solution for the Oral Cavity for Nebulization

| Benzalkonium chloroiodite | 25 mg |
| Menthol | 25 mg |
| Thymol | 12 mg |
| Camphor | 6 mg |
| Ethanol | 3 ml |
| Tween 20 | 1 ml |
| Distilled water | to 100 ml |

EXAMPLE 6

Spray-disinfectant Solution for Small Wounds and Abrasions

| Benzalkonium chloroiodite | 100 mg |
| Absolute alcohol | 15 g |
| Brilliant green | 15 mcg |
| Tween 20 | 2 ml |
| Propellant (freon) | 85 g |

EXAMPLE 7

Solution for the Disinfection of Small Wounds and Abrasions and Areas of Skin for Hypodermic Injection

| Benzalkonium chloroiodite | 100 mg |
| Tween 20 | 2 ml |
| Absolute | 10 ml |
| Brilliant green | 300 mcg |
| Distilled water | to 100 ml |

EXAMPLE 8

Disinfectant Cloths

Each 'cloth' consists of a non-woven cellulose tampon drenched with 2 ml of solution having the following composition:

| Benzalkonium chloroiodite | 2 mg |
| Absolute Alcohol | 160 mg |
| Brilliant green | 6 mcg |
| Tween 20 | 40 mg |
| Distilled water | to 2 ml |

EXAMPLE 9

Disinfectant Sweets for the Oral Cavity

| Benzalkonium chloroiodite | 1 mg |
| Sugar, dyestuffs, aromatizers | to 2.5 g |

EXAMPLE 10

Disinfectant Sweets for the Oral Cavity (for Diabetics)

| Benzalkonium chloroiodite | 1 mg |
| Xylitol, dyestuffs, aromatizers | to 2.5 g |

EXAMPLE 11

Chewing-gum for Disinfecting the Oral Cavity

| Benzalkonium chloroiodite | 1 mg |
| Sugar, acacia, glycerine, butylhydroxytoluene and chewing-gum base | to 2.5 g |

EXAMPLE 12

Chewing-gum for Disinfecting the Oral Cavity (for Diabetics)

| Benzalkonium chloroiodite | 1 mg |
| Sorbitol, mannitol, acacia, mint butylhydroxy toluene, glycerine and chewing-gum base | 2.5 g |

EXAMPLE 13

Deodorant Spray

| Isopropyl myristate | 3 g |
| Ethanol | 3 g |
| Benzalkonium chloroiodite | 0.25 g |
| Freon 114 | 18.75 g |
| Freon 12 | 75.00 g |

EXAMPLE 14

Detergent Emulsion for Intimate Hygiene

| Texapon MLS | 25 g |
| Dehyton AB 30 | 8 g |
| Citric acid | 0.2 g |
| Perfume | 0.2 g |
| Benzalkonium chloroiodite | 0.3 g |

| -continued | |
|---|---|
| Distilled water | 66.30 ml |
We claim:
1. Benzalkonium chloroiodite, a compound of the formula:
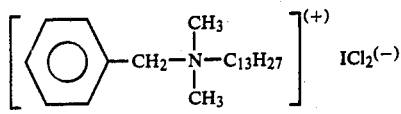
2. A pharmaceutical composition containing as active ingredient a bactericidally effective amount of benzalkonium chloroiodite of the formula of claim 1 together with a pharmaceutical carrier or excipient.
* * * * *